United States Patent [19]

Cipolla

[11] Patent Number: 5,616,141
[45] Date of Patent: Apr. 1, 1997

[54] LASER SYSTEM FOR USE IN DENTAL PROCEDURES

[75] Inventor: Anthony J. Cipolla, Cogan Station, Pa.

[73] Assignee: Ion Laser Technology, Salt Lake City, Utah

[21] Appl. No.: 584,752

[22] Filed: Jan. 11, 1996

Related U.S. Application Data

[63] Continuation of Ser. No. 377,678, Jan. 24, 1995, abandoned, which is a continuation of Ser. No. 45,967, Apr. 9, 1993, abandoned.

[51] Int. Cl.$^6$ ........................................................ A61H 5/06
[52] U.S. Cl. ................................ 606/15; 606/2; 433/29; 433/141; 433/215; 433/226
[58] Field of Search ................ 606/2, 3–19; 433/29–31, 433/141, 146, 147, 215, 224, 226, 229

[56] References Cited

U.S. PATENT DOCUMENTS

| | | | |
|---|---|---|---|
| 4,069,823 | 1/1978 | Isakov et al. | 128/303.1 |
| 4,608,980 | 4/1986 | Aihara | 606/16 |
| 4,826,431 | 5/1989 | Fujimura et al. | 433/29 |
| 4,940,411 | 7/1990 | Vassiliadis et al. | 433/215 |
| 5,051,823 | 9/1991 | Cooper et al. | 358/98 |
| 5,055,048 | 10/1991 | Vassiliadis et al. | 433/215 |
| 5,123,845 | 6/1992 | Vassiliadis et al. | 433/215 |

FOREIGN PATENT DOCUMENTS 152686  8/1985  European Pat. Off. ................ 606/16

OTHER PUBLICATIONS

"Insights and Innovations: Checking the Reliability of Your Curing Light," Howard E. Strassler, D.M.D., F.A.D.M., *Journal of Esthetic Dentistry*, vol. 4, No. 3, May/Jun. 1992, pp. 102 and 104.

"Dental and Oral Applications of the Argon Laser," *1990 Series Argon Laser Operator's Manual*, Sep. 20, 1991, pp. 7–17 through 7–78 with attached case reports.

"Clinical Effects of Closed Root Planing Compared to Papilla Reflection and fiber Optic Augmentation," Richard A. Reinhardt, Georgia K. Johnston, and Linda M. Dubois, *J Periodontal*, May 1991, pp. 317 through 321.

"Blue Laser Curing of Composites," Andrej Meniga, Jozo Sutalo, Davorka Azinovie, and Goran Pechler, *Acta Stomatologica Croatica* 1992, pp. 93 through 98.

"Degree of Composite Resin Polymerization with Visible Light and Argon Laser," Richard J. Blankenau, DDS; William P. Kelsey, DDS; G. Lynn Powell, DDS; Greg O. Shearer, MS, Ph.D.; Wayne W. Barkmeier, DDS, MS; & W. Thomas Caval, DDS; *American Journal of Dentistry*, vol. 4, No. 1, Feb. 1991, pp. 40 through 42.

"Post Polymerization Strength Values of an Argon Laser Cured Resin," R.J. Blankenau, DDS; G.L. Powell, DDS; W.P. Kelsey, DDS; & W.W. Barkmeier, DDS, MD; *Lasers in Surgery and Medicine*, 1991, pp. 471 through 474.

(List continued on next page.)

Primary Examiner—David M. Shay
Attorney, Agent, or Firm—Madson & Metcalf

[57] ABSTRACT

A laser system for use in performing dental procedures is provided. The system includes a handpiece which is capable of being connected to a source of laser light, such as a fiber optic cable. The fiber optic capable carries laser light into the handpiece. For most of the purposes contemplated herein, the argon laser light is preferred. The handpiece includes a collimating lens such that the laser light is collimated and a collimated laser output exits said handpiece. Collimated laser light is found to be useful in initiating the curing of dental resin restorative materials. Also placed within the handpiece is a mirror for controlling the direction of laser light output from said handpiece and for directing the collimated laser light toward a dental work area. Finally, multiple detachable attachments are provided which are capable of being mounted on the exterior or at the proximal end of said handpiece for optionally modifying said collimated laser light output. Such attachments may include lenses, optical filters, and fiber optic cables.

7 Claims, 5 Drawing Sheets

OTHER PUBLICATIONS

"Initial Caries Diagnosis in Rat Molars, Using Laser Fluorescence," Ulrika Hafström–Björkman, Folke Sandström & Birgit Angman–Månsson, *Acta Odontol Scand* 1991, pp. 27 through 33.

"Criteria for Substituting Amalgam with Composite Resins," J.F. Roulet and M.J. Noack, *International Dental Journal* (1991), pp. 195 through 205.

"Posterior Adhesive Composite Resin: A Historic Review," Takao Fusayama, D.D.S., Ph.D., *Journal of Prostethic Dentistry*, Nov. 1990, vol. 64, No. 5, pp. 534 through 538.

"Laser Photopolymerization of Dental Materials with Potential Endodontic Applications," Thomas v. Potts, DDS, Ph.D. and Athos Petrou, Ph.D., *Journal of Endodontics*, vol. 16, No. 6, Jun. 1990, pp. 265 through 268.

"Pulp Chamber Temperature Changes With Visible–Light–Cured Composites In Vitro," H.E. Goodis, J.M. White, B. Gamm, L. Watanabe, *Dental Materials*, Apr. 1990, pp. 99 through 102.

"Contributo Allo Studio Sulla Influenza Della Luce Laser Nella Polimerizzazione Dei Compositi," (Influence Of Light Laser Argon Technique On Composite Resin Polymerization), G. Calura, M. Nonato, M. Franchi, and M. Pagnanelli, *Minerva Stomatologica*, vol. 48, No. 4, Apr. 1989, pp. 395 through 403. This reference relates to a study verifying the advantages of laser argon techniques.

"Enhancement of Physical Properties of Resin Restorative Materials by Laser Polymerization," William P. Kelsey III, DDS, Richard J. Blankeneau, DDS, G. Lynn Powell, DDS, Wayne W. Barkmeier, DDS, W. Thomas Cavel, DDS, MS, and Brian K. Whisenant, BS, *Lasers in Surgery and Medicine*, 1989, pp. 623 through 627.

"Ipotesi Chimico–Fisiche Sulla Fissazione Del Fluoro Nello Smalto Mediante Luce Laser" (Chemico–Physical Hyoptheses on Fluoride Fixation in Enamel by Means of Laser Light), D. Palano, G. Molinari, *Minerva Stomatologica*, vol. 37, No. 12, pp. 923 through 927. This study relates to fluoride fixation using laser light.

"Dental Holography–Earlier Investigations and Prospective Possibilities," B.I. Dortoft, *Advanced Dental Res*, 1(1), Oct., 1987, pp. 8 through 13.

"Optical Methods to Measure Shape and Size," P.M. Boone, *Advanced Dental Res*, 1(1), Oct., 1987, pp. 27 through 38.

"Optical Methods for the Detection and Quantification of Caries," B. Angmar–Mänsson and J.J. Ten Bosch, *Advanced Dental Res*, 1(1), Oct., 1987, pp. 14 through 20.

"Laser Curing of Acrylic Coatings," C. Decker, *Radiation Curing of Polymers*, Special Publication No. 64, Sep. 18–19, 1986, pp. 16 through 31.

"Curing Depth of Visible Light–Activated Composites," Lennart Forsten, *Acta Odontol. Scand.*, 1984, pp. 23 through 28.

"Wavelength and Intensity of Seven Systems for Visible Light–Curing Composite Resins: a Comparison Study," Richard J. Blankenau, DDS, W. Patrick Kelsey, DDS, W. Thomas Cavel, Paul Blankenau, *JADA*, vol. 106, Apr. 1983, pp. 471 through 474.

"Post–Irradiation Polymerization of Visible Light–Activated Composite Resin," Leung, P.O. Fan, and W.M. Johnston, *J Dent Res*, Mar. 1983, pp. 363 through 365.

"Spectral Distributions of Dental Photopolymerization Sources," W.D. Cook, *J Dent Res*, 61(12), Dec. 1982, pp. 1436 through 1438.

"Chemistry, Composition, and Properties of Composite Resins," Robert G. Craig, Ph.D., *Dental Clinics of North America*, vol. 25, No. 2, Apr. 1981, pp. 219 through 239.

"The Light–Cure Phenomenon: How It Works," Eric H. Rommerdale, CDT and Aaron D. Puckett, PhD, *Modern Dentalab*, p. 52.

"Photocured Hydroxyapatite Composites for Dental and Medical Applications," Aaron Puckett, Mike Nichols, Angela Patrick, U. of Mississippi School of Dentistry, Robson Storey, Steve Warren, U. of Southern Mississippi, Mississippi Academy of Sciences Project, Jul./Aug. 1981, vol. 96, No. 2, pp. 19 and 20.

"Laser Photopolymerization of Dental Composites," A. Puckett and B. Bennett, Biomaterials, University of Mississippi Medical Center, Jackson, MS 39212

"Dental Laser Instruments & Accessories Catalog," ORALASE, a Division of HGM, Inc., Oct. 1, 1991. (6 pages).

"Dental Laser Systems Catalog," ORALASE, 1991. (4 pages).

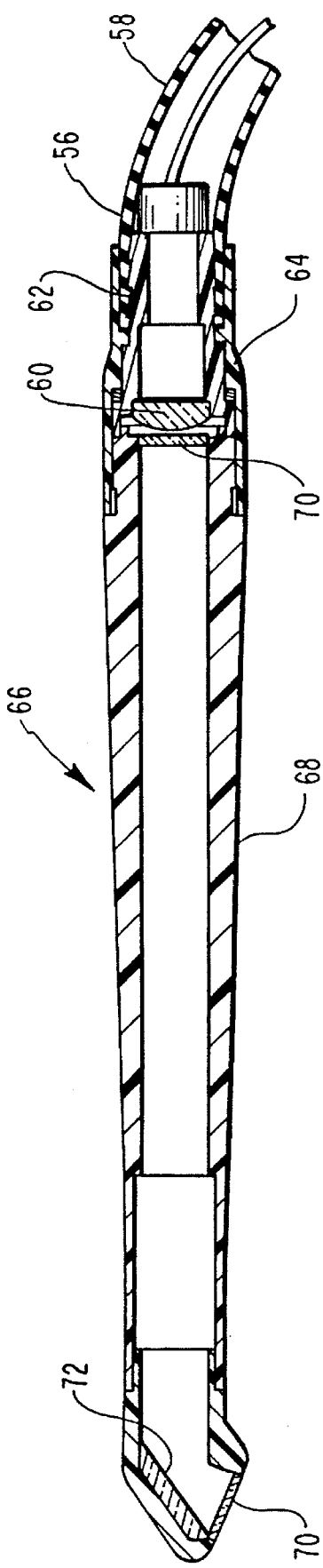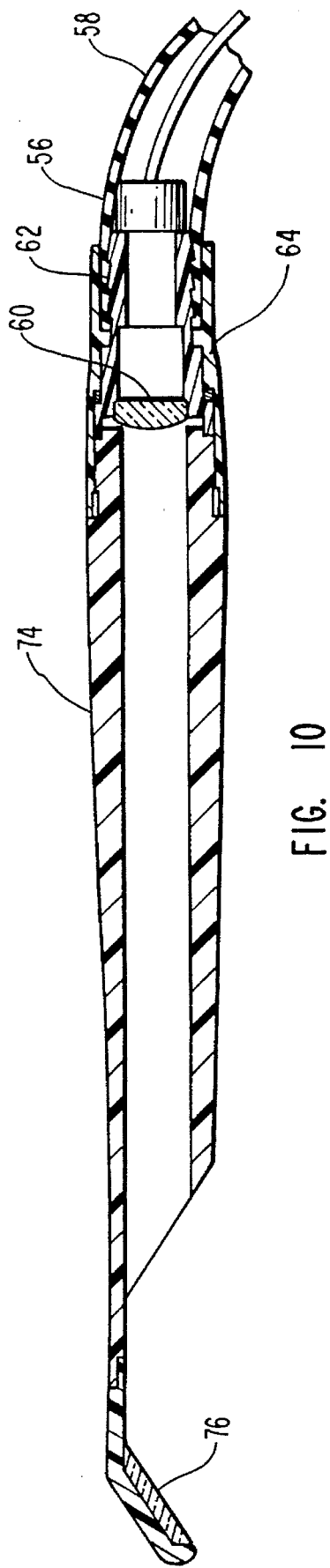
FIG. 9
FIG. 10

LASER SYSTEM FOR USE IN DENTAL PROCEDURES

This application is a continuation of U.S. application Ser. No. 08/377,678, filed Jan. 24, 1995, for LASER SYSTEM FOR USE IN DENTAL PROCEDURES now abandoned which is a continuation of application Ser. No. 08/045,967 filed Apr. 9, 1993 now abandoned.

BACKGROUND

1. The Field of the Invention

The present invention relates to a laser system for performing a variety of dental procedures, particularly curing of dental restoratives. More particularly, the present invention relates to a device which provides a collimated laser light output for use in dentistry, together with removable attachments for modifying the light output of the device.

2. Technical Background

Numerous recent improvements in dentistry have related to the manner in which conventional procedures are performed, as well as improved and expanded procedures available through improvements in technology. One significant area of advancement in dentistry has related to improvement in materials available for use in dental procedures. For example, modern dentists have available a wide scope of materials which have not been traditionally used in dentistry. While composite resin-based materials have been known for some time, they have had limited applicability to dentistry because of limitations in the characteristics of the materials. A particularly notable problem relates to the inability to adequately and uniformly cure these materials. In recent years, however, development of these materials has resulted in more acceptable dental materials, even though problems with curing continue.

Reactive composite resin materials of the type used in dentistry are generally classified as either condensation resins or addition resins. Condensation resins generally involve the reaction of two different chemical species to produce a final cured product. Addition resins, conversely, rely on the generation of an activated free radical which is added to the resin and which initiates the polymerization reaction.

Light cured resins are generally considered to be addition resins. In these systems light activates or decomposes a light sensitive molecule, which in turn initiates the polymerization reaction within the resin system. Some photoinitiator molecules which have been used in such systems include benzoin methyl ether, camphoroquinone, biacetyl, and acenaphthenequinone. These materials are well known and commercially available.

Typically, the photoinitiator used in the composite resin system is decomposed upon exposure to light of a specific wavelength. This provides significant advantages. For example, it is possible to work freely with the material until it is set in place. At that point, the material is exposed to light of a wavelength which will initiate cure. Thus, control over cure is maintained by the user.

In order to cure addition resin composite materials, the use of laser light has been suggested. The use of conventional light sources has resulted in generally inadequate curing in certain areas of its application because of the insufficient energy available from such conventional light sources.

Laser light has been found to have a number of advantages over conventional light sources. Laser light can be produced which is essentially monochromatic. Conventional light sources, conversely, contain a full spectrum of wavelengths. As a result, it is possible to chose a laser wavelength or wavelengths which correspond to specific wavelengths which trigger curing in the composite resin. Another advantage of laser light is that it is "coherent." That is, it forms a single integrated beam of light. This allows the light to be channeled through precision optics and focused into a fiber. In this manner, the beam as it exits the fiber is divergent. If the proper distance and spot size are maintained, it is possible for the laser light to provide sufficient energy to initiate the polymerization reaction of the composite resin.

Problems have been encountered even in the use of laser light initiated addition resin systems, such as the recurring problem of uneven cure. A number of factors may influence the adequacy of cure, including the nature of the composite resin system used, the shade of the composition, light exposure time, the type of light source used, the energy density of the light and the dimensions and other characteristics of the restoration. It will be appreciated that dealing with these factors presents the dentist with a difficult task.

The problem is made more difficult with the use of a divergent laser beam which occurs straight from the end of a fiber optic cable. Divergent beams are used in order to provide sufficient beam strength at a single point of interest. The limitation with this technique is that it is necessary for the dentist to manipulate the laser beam such that the proper spot, as it relates to the energy density, is placed at the desired location on the composite restoration in order to achieve adequate and even cure. This is difficult particularly in view of the fact that the laser light may be outside the visible spectrum or if the laser light fluoresces the material to be cured, thereby obscuring any definitive spot size. If adequate cure is not achieved (if there is a failure to fully polymerize the resin composite) it may result in retention failures, adverse pulpal responses, and a general decrease in the properties of the restoration.

Thus, while the use of composite resins has a number of appealing features, the actual use of these materials has been problematic. In particular, there have been significant drawbacks in the devices used to initiate cure. The limitations of these devices has resulted in inadequate and inconsistent curing of the composite resins. Clinically, this is seen as an incomplete cure, or poor bonding of resin to the tooth substrate especially down at the base of the cavity preparation. If the manipulated spot size is to large, inadequate cure may occur. If the manipulated spot size is too small, there exists a danger of dental pulpal injury, due to a hot energy density temperature rise. In addition, a manipulated small spot could cause a degradation in the filling material and its ability to bond to the tooth.

It would be an advantage in the art to provide a laser device which overcame the limitations identified above. At the same time, it would be beneficial to take advantage of the other possible uses of lasers in dentistry. For example, lasers have potential for use in dental surgery, including the cauterization of blood vessels. Lasers have been suggested for use in the place of scalpels in significant dental surgery. In addition, it is possible to use laser light in endodontic procedures.

Accordingly, it would be a significant advancement in the art to provide a device which was capable of overcoming the limitations now experienced in the delivery of laser light for use in dental procedures. In particular, it would be a significant advancement in the art to provide a device capable of delivering laser light having constant power along the beam, rather than a divergent beam. In that regard it would be an advantage to provide such a device which was capable of achieving consistent curing of dental restoratives. It would also be a significant advancement in the art to provide means for performing several different functions with a single source of laser output.

Such methods and apparatus are disclosed and claimed herein.

BRIEF SUMMARY AND OBJECTS OF THE INVENTION

The present invention is related to a laser system for use in performing various types of dental procedures, including specifically the curing of dental composite resin materials. The device of the present invention includes a dental handpiece. The handpiece is configured in the same general shape and size as standard dental instruments.

The dental handpiece includes an internal attachment for placing the handpiece in communication with a source of laser light, namely the terminus of a fiber optic cable. The fiber optic cable terminates within a portion of the handpiece. As the laser light exits the fiber optic cable it passes through a collimating lens positioned within the handpiece. This beam then exits the handpiece.

As a result of the structure of the present invention, a laser beam of constant cross section is produced. This beam also has relatively constant power over its usable length. This is a significant advantage over conventional devices. Conventional devices diverge the laser beam in order to achieve adequate energy density at a single point. It is difficult, however, to manipulate the focal point so that even cure is achieved. With the present invention precise positioning of the handpiece is not required because of the collimated nature of the laser output.

Also placed within the handpiece is means for controlling the direction of laser light output from the handpiece and for directing the laser light toward a dental work area. This may, for example, comprise one or more mirrors for directing the laser light from the interior of the handpiece onto the desired dental work area. Importantly, the light remains collimated and is not focused or diverged by the means for directing the light output.

Another significant advancement provided by the present invention is a disposable or sterilizable sleeve which can receive the handpiece described above. The present invention would allow for the utilization of a removable, sterilizable handpiece, separated at its proximal end (fiber optic cable end) from the collimated optics and handpiece nut. Multiple sleeves may be provided which contain different types of optical elements for optionally modifying laser light output in a specific desired manner. These sleeves constitute multiple detachable attachments capable of being mounted on the exterior of the handpiece. For example, the sleeve may include a filter which is positioned over the output window of the handpiece. In this way, it is possible to more accurately select the wavelength of the light output from the device.

Alternatively, the attachment may include a focusing lens. Using a focusing lens it is possible to use the same device for surgical procedures, and then remove the focusing lens to perform curing functions. Similarly, it is possible to add a fiber optic connector as an attachment. Using this type of device it is possible, for example, to connect the laser output to an endodontic fiber optic and perform certain endodontic procedures with the device.

In addition, one of the attachments may comprise a simple dental contact instrument attachment. This attachment may be added without modifying the collimated laser output of the device. This attachment is useful in manipulating the restorative or for performing other types of conventional dental manipulations, while at the same time maintaining the availability of immediate collimated laser output.

Finally, all handpiece functions could be done by using different removable sterilizable handpieces connected at the proximal end to the collimated optics and standard dental handpiece nut. All handpieces could be removed from the collimated optics connected with a single screw attachment or slip fit snap in connection. The collimated optics would be incorporated within the dental handpiece and would not be sterilized. The removable handpiece, in this case, could have different functional sleeves, or one could simply utilize separate functional handpieces. The change would take place by a sleeve change on the removable handpiece or by separate individual handpiece.

As mentioned above, the fiber optic which terminates within the handpiece is placed in communication with a source of laser light. It is presently preferred that this laser source be an argon laser. Argon lasers are presently preferred because the laser output of such lasers is of wavelengths which are capable of initiating cure. These wavelengths include 457.9 nm., 468 nm., 476.5 nm., 488 nm., and 496 nm.

Using the device of the present invention, it is simple to facilitate the cure of activated composite dental resin restorative materials. This process involves placing a sufficient quantity of light activated dental resin restorative material at a chosen location and then directing an output of collimated laser light onto the dental resin for a sufficient time to effect curing of the dental resin restorative. As mentioned above, the wavelength of the laser light is selected such that it is suitable for use in activating curing of the dental resin and preferably originates from an argon laser.

Accordingly, it is a primary object of the present invention to provide a device which is capable of overcoming the limitations now experienced in the delivery of laser light for use in dental procedures.

More particular, it is an object of the present invention to provide a device capable of delivering laser light having constant power along the beam, rather than a focused or divergent beam.

It is also an object of the present invention to provide means for performing several different functions with a single source of laser output.

These and other objects and advantages of the invention will become apparent upon reading the following detailed description and appended claims, and upon reference to the accompanying drawings.

BRIEF DESCRIPTION OF THE DRAWINGS

In order to more fully understand the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 9 is a longitudinal cross sectional view of an alternative embodiment of the invention comprising a removable handpiece.

FIG. 10 is a longitudinal cross sectional view of a further embodiment of the device having a removable handpiece attached to a standard set of fiber optics.

DETAILED DESCRIPTION OF THE PREFERRED EMBODIMENTS

Figure 1:
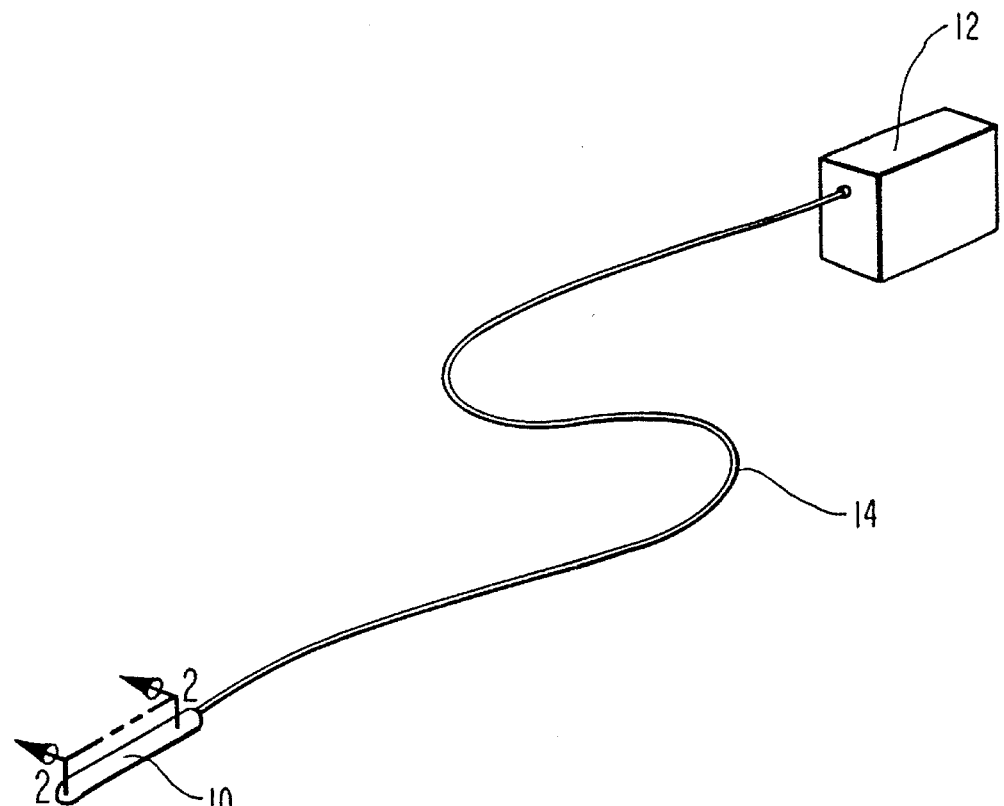
FIG. 1 is a perspective view of the dental laser handpiece of the present invention connected to an argon laser by means of a fiber optic cable.

The present invention can be best understood by reference to the drawings where like parts are designated with like numerals throughout. FIG. 1 shows the dental laser handpiece 10 of the present invention connected to a argon laser 12 by means of a fiber optic cable 14. The laser may, for example, comprise an argon ion laser. As mentioned above, the present invention provides convenient means for delivering laser light for dental applications.

Various types of lasers may be used in different dental applications; however, argon lasers have been found to be particularly adaptable when curing of composite resin materials is desired. Argon lasers are known to provide laser light outputs generally in the blue-green portion of the spectrum, and these outputs are found to be ideally suited for this type of dental application. Specifically, the argon ion laser is known to produce strong bands in the 457.9 nm., 468 nm., 476.5 nm., 488 nm., and 496 nm. regions. Acceptable argon lasers of this type are available commercially. One example is the Model 5500 AWC-00 available from Ion Laser Technology, Salt Lake City, Utah.

As mentioned above, the output of the laser 12 is directed into a conventional fiber optic cable 14. Again, suitable fiber optic cables and couplers of this type are well known and commercially available. Suppliers of such fiber optic cables include Fiberguide Industries and 3 M Specialty Fibers. In this manner, the laser light output of the laser 12 is transported in a readily controllable manner through the fiber optic cable 14 to the dental handpiece 10 for use by the dentist.

Figure 2:
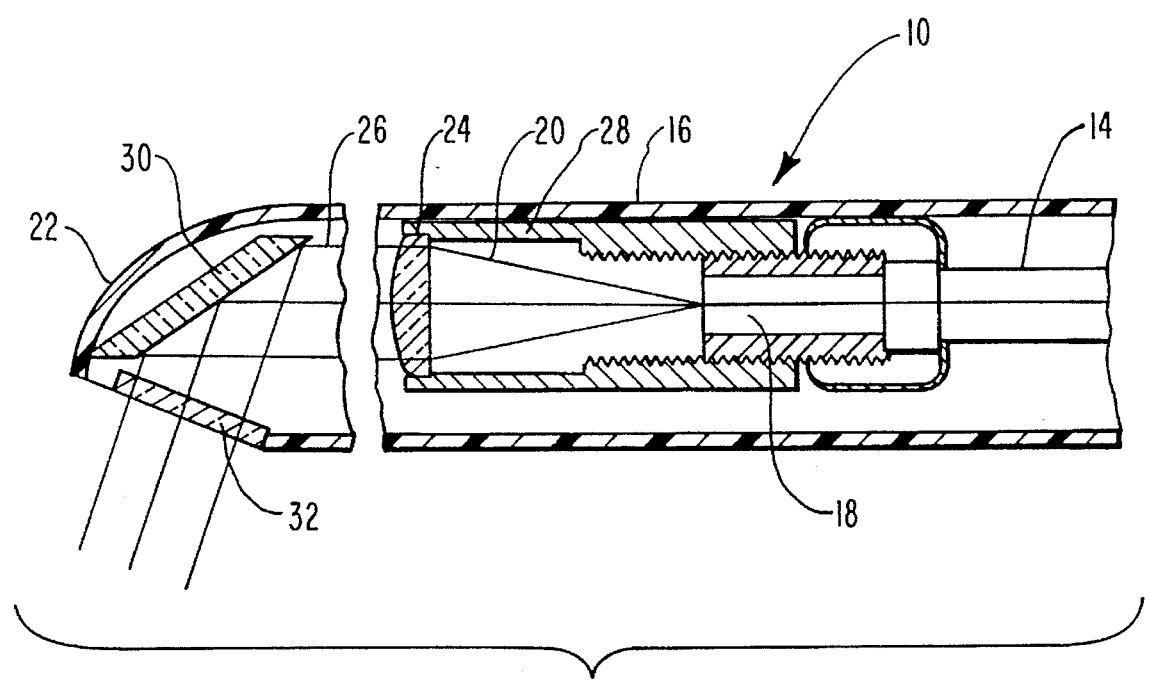
FIG. 2 is a longitudinal cross sectional view of the handpiece along line 2—2.

The manner of operation of the dental handpiece 10 can be more fully appreciated with reference to FIGS. 2–10. Referring specifically to FIG. 2, a longitudinal cross sectional view of the handpiece core 16 is provided. As can be seen in FIG. 1, the fiber optic cable 14 terminates within the interior of the handpiece core 16. The fiber optic terminus 18 is securely mounted within the handpiece core 16 by conventional means, such as the threaded mechanism illustrated in FIG. 2.

With continuing reference to FIG. 2, laser light 20 exits the fiber optic cable 14 and is directed toward the front 22 of the handpiece 10. As the light exits the fiber optic cable 14, it tends to disperse. Accordingly, it is necessary to provide optics for capturing the laser light output 20 and placing it into a usable form. For the purposes of the present invention, collimated light is preferred. Accordingly, the light 20 is passed through a collimating lens 24. The collimating lens 24 takes the laser light 20 and converts it into a parallel collimated beam 26 of constant cross section. Again the collimating lens 24 is mounted within the handpiece by conventional means, such as by lens support 28. Collimating optics assemblies are commercially available from a variety of commercial sources, including NSG America, Inc.

The collimated laser beam 26 continues to travel toward the front 22 of the handpiece 10 where it encounters means for controlling the direction of the laser light 20 as it exits the handpiece 10 and for directing the laser light output 20 toward a desired dental work area. In the illustrated embodiment, this means for controlling the direction of the laser output comprises a mirror 30. The mirror 30 is positioned such that it is capable of reflecting the collimated laser beam 26 through the exit window 32 and out of the handpiece 10. The exit window 32 is comprised of a piece of optical quality glass which allows the passage of the laser light beam 26 without distortion, but which protects and encloses the interior of the handpiece 10.

By the use of the handpiece core 16 it is possible to receive the output of the argon laser 12, and to place that output into a useable collimated laser beam 26. As discussed above, the use of collimated light 26 has a number of significant advantages in dental applications. In particular, the availability of a collimated laser light output 26 allows curing to take place without the uncertainties and uneven curing experienced using conventional methods in that collimated light 26 has constant power and cross section over its useable length.

Figure 3:
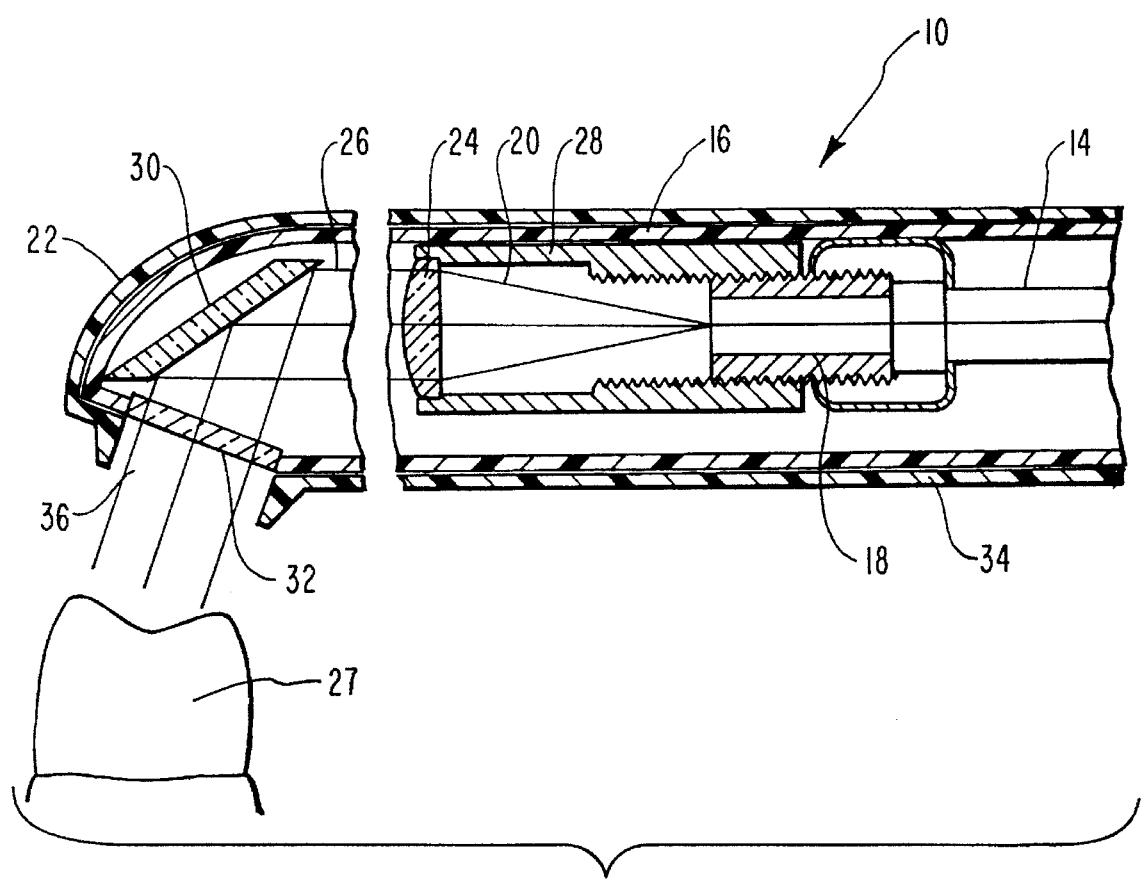
FIG. 3 is a longitudinal cross sectional view similar to FIG. 2, showing the handpiece surrounded by a detachable sleeve.

In actual practice, it will be desirable to enclose the handpiece core 16, to protect it from damage, and to isolate the handpiece core 16 from the work area. This is accomplished by means of a disposable or sterilizable sleeve 34 as illustrated in FIGS. 3–8. Reference is made to FIG. 3 where the sleeve 34 is configured such that the handpiece core 16 fits securely within the interior of the sleeve 34. At the same time, the sleeve 34 is provided with an opening 36 which corresponds to the window 32, through which the laser light 20 exits the handpiece core 16. Thus, the sleeve is able to protect the handpiece core 16 while not obstructing the output of laser light 20. At the same time, the sleeve 34 may be constructed such that it is easily gripped and manipulated by the dental professional. The sleeve 34 may be constructed of easily disposable medical grade plastic materials, or it may be constructed of sterilizable materials such as stainless steel.

FIG. 3 illustrates the general method by which the collimated light output is used to cure a dental restorative. In FIG. 3, the collimated beam 26 is directed onto a tooth 27 which has been repaired using an resin material. It will be appreciated that the initiation of the cure has been simplified by the present invention in that the collimated beam 26 has relatively constant power over its usable length. Thus, fine manipulation of the handpiece 10 may not be as critical as has been the case with conventional devices.

Figure 4:
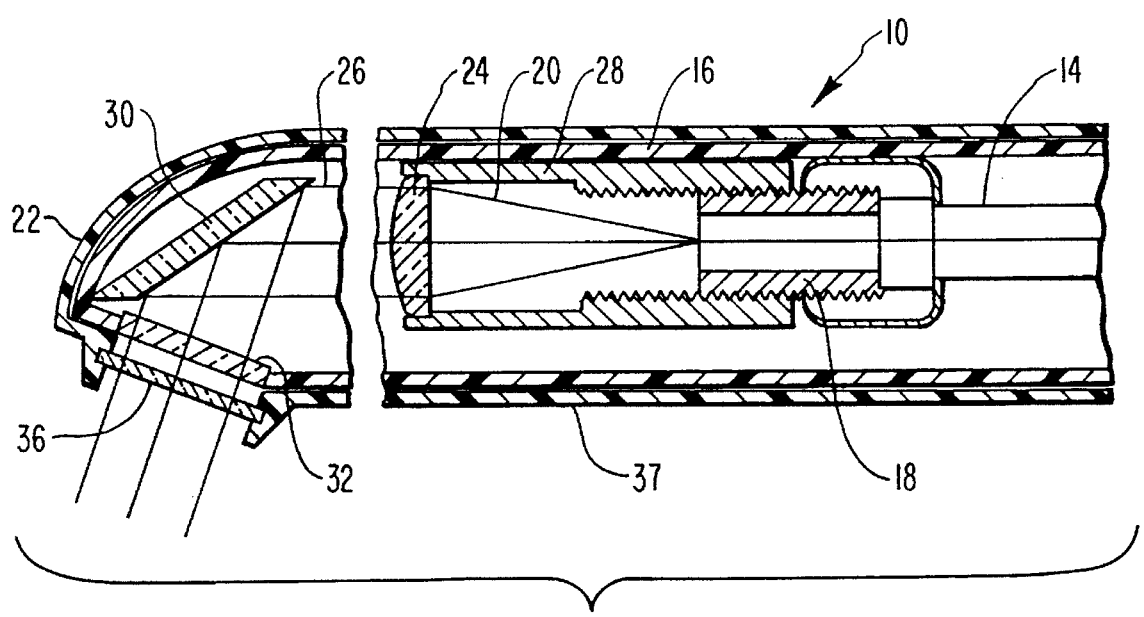
FIG. 4 is a longitudinal cross sectional view of the handpiece surrounded by a detachable sleeve, which sleeve carries an optical filter.

The sleeve 34 may be modified to perform a variety of significant functions. Indeed, it is presently preferred to provide a series of sleeves which comprise multiple detachable attachments to the dental laser handpiece 10. For example, FIG. 4 illustrates the handpiece 10 surrounded by a sleeve 37 in the same generally manner as described with reference to FIG. 3. In this embodiment, however, the sleeve 37 is equipped with a filter 36. The filter 36 may be chosen such that light of only a single specific wavelength exits the device 10, or may make other desired modifications to the light output 10. Thus, it is possible to provide a collimated laser output 26 at a specific wavelength such that curing of composite resin materials is initiated in an efficient and controlled manner.

In some contexts, it will be desirable to use this device for surgical procedures, as well as for curing of composites. When this is the case, it will be necessary to modify the collimated light output 26 of the handpiece 10 for the particular application. Thus, sleeves may be provided which expand the detachable attachment function of the invention by including light modification devices on the sleeve.

Figure 5:
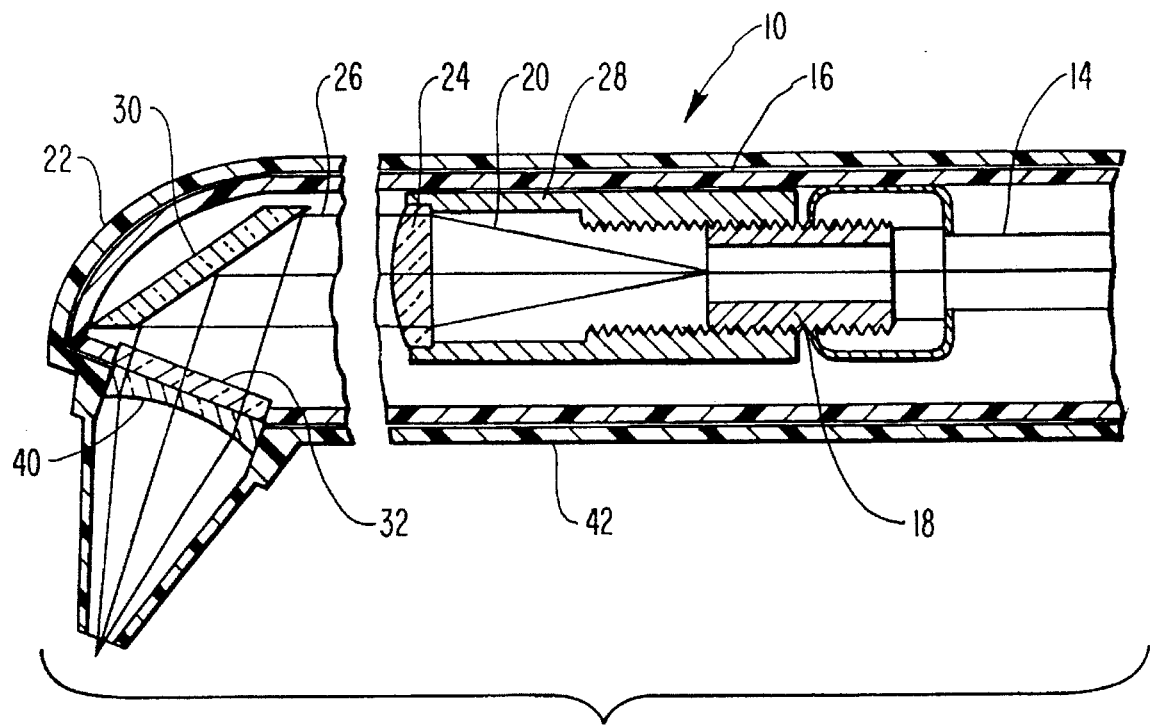
FIG. 5 is a longitudinal cross sectional view of the handpiece surrounded by a detachable sleeve, which sleeve carries a focusing lens.

One example is illustrated in FIG. 5. In FIG. 5, the sleeve 42 is provided with a focusing lens 40. As the light exits the window 32 it passes through the focusing lens 40 to provide a powerful focused output. The laser light output 20 from this embodiment of the device is capable of use in surgical procedures such as oral surgery, endodontic procedures, and cauterization of blood vessels.

When the surgical procedure is completed, the sleeve 42 and the focusing lens 40 can be removed. At this point, it may be desirable to perform other dental functions. For example, it may then be necessary to cure a dental restorative material. If this is the case, sleeve 34 or 37 are easily installed such that a collimated beam 26 is provided to initiate cure. Alternatively, the other sleeves discussed below may be used to perform various other types of dental procedures. In any event, it will be appreciated that the handpiece core 16 is made adaptable to provide a variety of functions.

Figure 6:
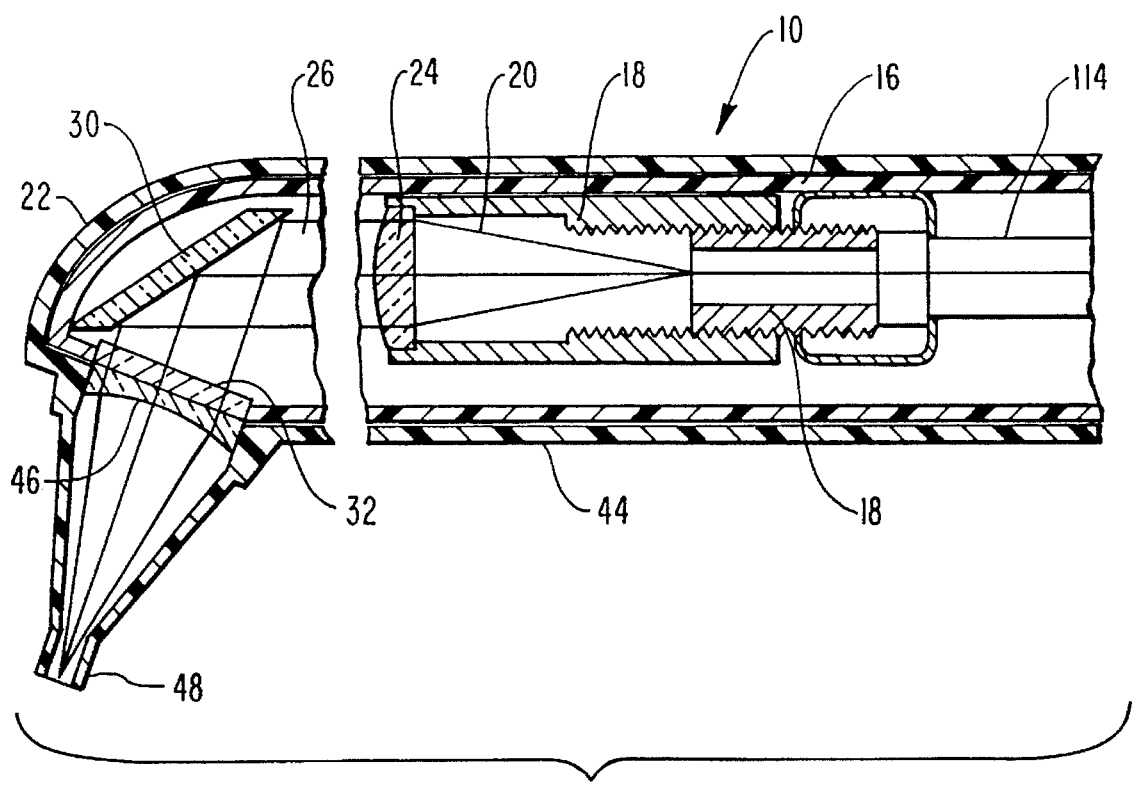
FIG. 6 is a longitudinal cross sectional view of the handpiece surrounded by a detachable sleeve, which sleeve carries a focusing lens along with a fiber connector.

In certain applications, it may be desirable to direct the laser output into a further fiber optic cable such that it can be provided in small and hard to reach spaces. FIG. 6 illustrates one embodiment of a detachable attachment (i.e. sleeve) which performs this function. Sleeve 44 illustrated in FIG. 6 is placed on the handpiece core 16 in the same manner as discussed above. Sleeve 44 is equipped with both a focusing lens 46 and a fiber optic connector 48. By employing this structure it is possible to direct a focused laser output 20 into to a fiber optic cable for use in contact surgery illumination, and curing in hard to reach areas. This is a significant benefit in that conventional dental laser devices to not provide these capabilities in conjunction with providing easily accessible collimated light.

Figure 7:
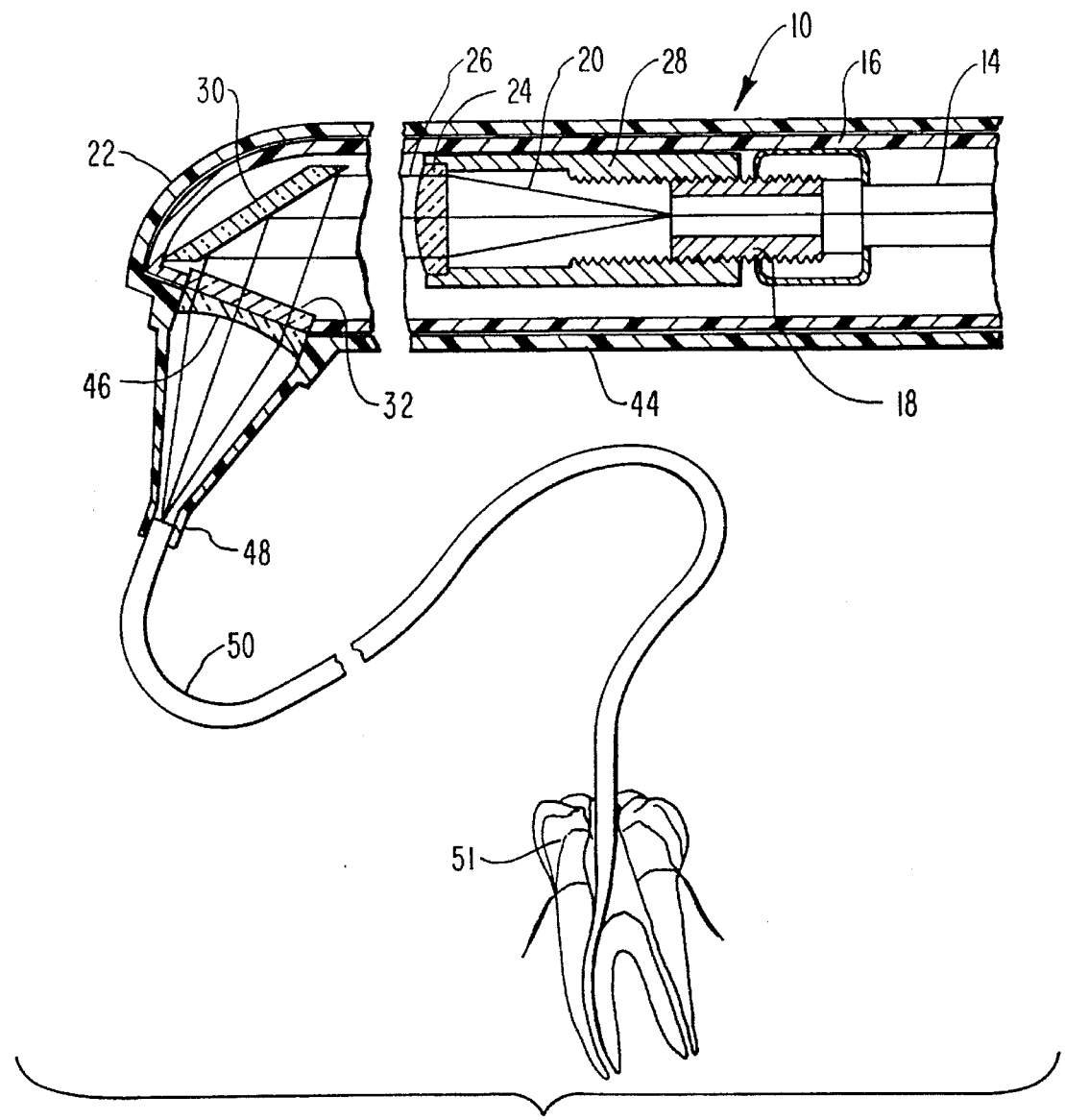
FIG. 7 is a longitudinal cross sectional view of the handpiece surrounded by a detachable sleeve illustrating the use of the device in endodontics.

FIG. 7 illustrates further the embodiment of the device shown in FIG. 6 In FIG. 7 a fiber optic cable 50 is connected to the fiber optic connector 48. The fiber optic cable 50 then carries the laser light output 20 to the desired location. As illustrated in FIG. 7, that area may comprise an endodontic work area 51. In this manner, the same device 10 which is ideally adapted to initiated curing of dental composites is also readily usable for other dental curing procedures such as endodontic curing of root canal fiber optic master cone fillings.

Figure 8:
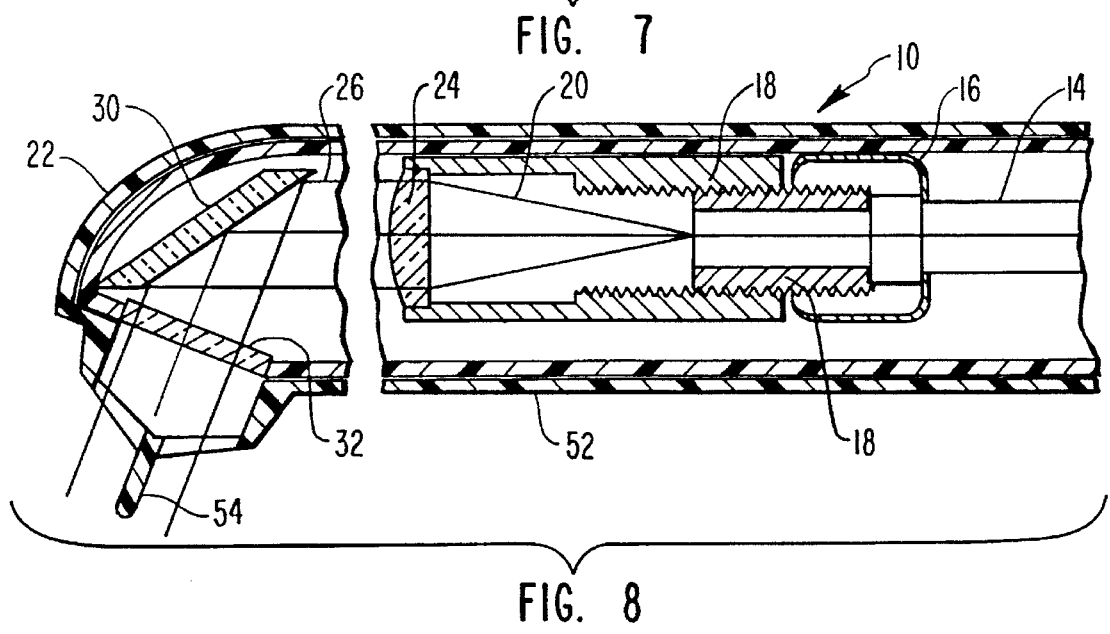
FIG. 8 is a longitudinal cross sectional view of the handpiece surrounded by a detachable sleeve which includes a dental contact instrument.

A further detachable attachment within the scope of the present invention is illustrated in FIG. 8. In FIG. 8, the sleeve 52 is equipped with a dental packing instrument 54. When this attachment is in place, the collimated laser light output 26 still exits the device in the manner described above. The dental packing instrument 54 does not significantly interfere with the collimated beam 26. The packing instrument 54, however, provides the dental professional with the capability of manipulating the restorative material or other materials in the mouth, before, during, and after the initiation of curing.

FIG. 9 is an alternative embodiment of the present invention. In this embodiment, the primary optical elements of the device are provided in a universal base unit 56. The universal base unit provides a terminal point for a fiber optic cable 58. As with the embodiments of the invention described above, the laser light which exits the fiber optic cable 58 is directed through a collimating lens 60. The collimating lens 60 is held in place by a lens support 62 which is placed within the universal base unit 56. The universal base unit 62 also includes a standard base nut 64, or similar structure, which is capable of removably attaching the universal base unit 62 to a removable attachment of the desired type.

One type of removable attachment is illustrated in FIG. 9 and is designated generally as 66. The attachment 66 is comprised of a removable handpiece 68 and the necessary optics. In the illustrated embodiment, the handpiece 68 includes a pair of sealed windows 70 on both ends of the handpiece 68. These windows protect the interior of the handpiece, and may be chosen Such that they modify the characteristics of the laser light output in some desirable manner.

The handpiece 68 also includes a mirror 72. The mirror 72 performs the same function as the mirrors described above. That is, the mirror provides means for directing the laser light output in the desired direction.

FIG. 10 illustrates a slightly different configuration of the device. This embodiment is also based on the universal base unit 56. The handpiece 74 is simply shaped differently. The handpiece 74 also includes a mirror 76 for directing the output from the universal base unit 56. This configuration of the device is more maneuverable and could find application in curing resin restoratives.

As discussed above, the present invention provides an improved process for curing visible light activated composite dental resin restorative materials. The process essentially involves placing a sufficient quantity of light activated dental resin restorative material at the chosen location in the mouth. The collimated laser light 26 from the device 10 is then directed onto the dental resin for a sufficient time to effect curing of the dental resin restorative. As mentioned above, the laser light 20 preferably originates from an argon laser such that the laser light 20 is selected such that it has a wavelength which activate curing of the dental resin.

The present invention provides a significant advantage over other laser curing systems in that a collimated beam 26 is provided. As mentioned above, collimated light 26 is preferable because it is of generally constant power over its cross section and usable length. By the use of collimated light 26 it is possible to avoid inconsistent curing and the problems which inconsistent curing causes. For example, unlike using conventional laser devices, it is not necessary for the dentist to precisely estimate where the focal point of the light is and perform the accompanying manipulation of the device such that the precise focal point contacts the restorative material. Rather significant leeway is provided by the present invention because the light does not have a focal point and the power of the light 20 output is relatively constant. In this manner, a constant power source contacts the restorative and is able to penetrate the restorative to initiate consistent curing.

It will be appreciated that the present invention accomplishes each of the objectives set forth above. The present invention is capable of overcoming significant limitations now experienced in the delivery of laser light for use in dental procedures. As discussed above, the device is capable of delivering laser light having constant power along the beam, rather than a focused or divergent beam. At the same time, the device provides means for performing several different functions with a single source of laser output. Thus, there is increased flexibility with the present invention.

The invention may be embodied in other specific forms without departing from its spirit or essential characteristics. For example, as previously mentioned, the sleeves used for sterilizability and function changes could be substituted by the use of separate handpiece. The embodiments could relate to FIGS. 9 and/or 10. The essential part of the art for ensuring a consistent even cure is maintained by the utilization of the collimated optics. In the design, the collimated optics would be maintained in the proximal end of the handpiece situated in the standard dental handpiece nut. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for curing dental composite material having a light activated cure mechanism comprising the step of directing a beam of substantially collimated laser light toward said dental composite material such that curing of said composite material is initiated, said laser light being selected such that it has a wavelength greater than 400 nm.

2. A method for curing dental composite material as defined in claim 1 wherein said laser light originates from an argon laser.

3. A method for curing dental composite material as defined in claim 1 wherein said source of laser light has light with wavelengths selected from the group consisting of 457.9 nm., 468 nm., 476.5 nm., 488 nm., and 496 nm.

4. A process for curing visible light activated composite dental resin restorative materials, comprising the steps of:

placing a sufficient quantity of light activated dental resin restorative material at a site of dental repair;

directing an output of substantially collimated laser light onto said quantity of dental resin for a sufficient time to effect curing of the dental resin restorative, said laser light being selected such that the laser light has a wavelength greater than 400 nm and the wavelength activates curing of said dental resin.

5. A process for curing dental resin restorative materials as defined in claim 4 wherein said laser light originates from an argon laser.

6. A process for curing dental resin restorative materials as defined in claim 4 wherein said source of laser light has light with wavelengths selected from the group consisting of approximately 457.9 nm., 468 nm., 476.5 nm., 488 nm., and 496 nm.

7. A process for curing dental resin restorative materials as defined in claim 4 wherein said collimated light is provided by a laser device for curing ceramic dental materials comprising a dental handpiece; a source of laser light in communication with said dental handpiece and terminating within a portion of said handpiece; means within said handpiece for collimating said laser light such that a collimated laser output exits said handpiece; means within said handpiece for controlling the direction of laser light output from said handpiece and for directing said laser light toward a dental work area such the laser beam which exits said dental handpiece has substantially constant power over the effective length of the beam, such that curing of said ceramic dental materials can be initiated substantially evenly.

\* \* \* \* \*